United States Patent [19]

Manser et al.

[11] Patent Number: 5,463,019
[45] Date of Patent: Oct. 31, 1995

[54] POLYMERS AND COPOLYMERS FROM 3-AZIDOMETHYL-3-NITRATOMETHYLOXETANE

[75] Inventors: Gerald E. Manser, El Dorado Hills; Aslam A. Malik, Cameron Park; Thomas G. Archibald, Fair Oaks, all of Calif.

[73] Assignee: Aerojet-General Corporation, Sacramento, Calif.

[21] Appl. No.: 377,572

[22] Filed: Jan. 23, 1995

Related U.S. Application Data

[63] Continuation-in-part of Ser. No. 940,269, Sep. 2, 1992, abandoned.

[51] Int. Cl.$^6$ .................. C08G 65/22; C07D 305/06; C07C 43/10
[52] U.S. Cl. .................. 528/402; 528/417; 549/510; 549/511; 568/615; 568/620
[58] Field of Search .................. 528/417, 402; 568/620, 615; 549/510, 511

[56] References Cited

U.S. PATENT DOCUMENTS

| | | | |
|---|---|---|---|
| 4,806,613 | 2/1989 | Wardle | 528/59 |
| 4,952,644 | 8/1990 | Wardle | 525/410 |
| 4,988,797 | 1/1991 | Wardle | 528/417 |
| 5,099,042 | 3/1992 | Wardle | 528/417 |
| 5,210,153 | 5/1993 | Manser | 528/417 |
| 5,214,166 | 5/1993 | Manser | 549/510 |

*Primary Examiner*—John C. Bleutge
*Assistant Examiner*—D. R. Wilson
*Attorney, Agent, or Firm*—Townsend and Townsend and Crew

[57] ABSTRACT

3-Azidomethyl-3-nitratomethyloxetane, a novel oxetane compound, is used as a monomer for the formation of homopolymers and copolymers with other known energetic oxetane monomers. The polyethers of the present invention can be subsequently cured to form elastomers suitable for use as energetic binders in propellant formulations or the like.

19 Claims, No Drawings

POLYMERS AND COPOLYMERS FROM 3-AZIDOMETHYL-3-NITRATOMETHYLOXETANE

STATEMENT OF GOVERNMENT INTEREST

This invention was made with Government support pursuant to Contract No. N00l4-89-C-0281 awarded by the Department of the Navy. The Government has certain rights in this invention. This application is a continuation-in-part of Ser. No. 07/940,269, filed Sep. 2, 1992, now abandoned.

FIELD OF THE INVENTION

The present invention is directed to novel polyethers, particularly for use in binder formulations for high-energy, nitrate ester plasticized propellants. More specifically, this invention relates to the synthesis and polymerization of 3-azidomethyl-3-nitratomethyloxetane (AMNO).

BACKGROUND OF THE INVENTION

High-energy solid formulations, such as propellants, explosives, and gasifiers, generally consist of particulate solids, such as fuel material, oxidizers, or both, held together by an elastomeric binder. These formulations may also include a liquid plasticizer, such as a nitrate ester, which contributes to the elastomeric characteristics of the binder and adds additional energy to the formulation.

While the elastomeric binder matrix is an important means of dispersing and immobilizing the fuel material and oxidizer, the materials used in the binder burn with substantially lower energy than does the fuel material. The binder thus imposes a limit on the energy content available from the fuel material. One way to minimize this limitation is to use an elastomeric binder which releases as much energy as possible when burning with the fuel material. It is desirable, therefore, that the elastomeric binder have pendant groups which themselves are relatively high in energy.

Plasticizers are used in solid propellants and explosives to facilitate processing and increase flexibility and toughness, in addition to providing other benefits which vary with the nature and use of the formulation. Energetic or high-energy plasticizers are those that provide energy in addition to flexibility and toughness, and their inclusion therefore does not lessen the performance of the formulation. Considerations involved in the selection and use of plasticizers include compatibility with the other components of the formulation, including the primary energetic compounds and any binders present, the oxygen balance of the plasticizer, energy content, safety (i.e., stability with regard to detonation) and melting point. Plasticizers with melting points in a range which causes them to crystallize readily, for example, are of limited utility, since crystallization is detrimental to the plasticizer function and can adversely affect the mechanical properties of the propellant or explosive.

If a nitrate ester plasticizer is included in the formulation, it is desirable that the elastomeric binder be compatible with the nitrate ester plasticizer, i.e., nitroester-miscibility is required. If the binder system is insufficiently miscible with the nitrate ester plasticizer, the plasticizer will weep or flow and settle out from the binder. Certain polymers which have sufficiently high energies and would otherwise be useful elastomers for binders cannot be used in certain binder systems because they are incompatible or immiscible with the nitrate ester plasticizer. Polyethers prepared from tetrahydrofuran (THF) are examples of such polymers. These polyethers have sufficiently high energies, high load-bearing capabilities, and low glass transition temperatures ($T_g$'s), but because they are immiscible with nitrate esters, they cannot be used in binder systems which utilize nitrate ester plasticizers. In addition to being high in energy, therefore, the polyethers and the elastomers formed therefrom should contain pendant groups which impart miscibility of the elastomers with nitrate ester plasticizers. Nitro, nitrato, nitroamino and cyano groups are examples of pendant groups which impart nitrate ester-miscibility to the polymer and have relatively high energies so as to contribute to the performance of the propellant.

In view of the foregoing, there exists a need for novel polyether polymers which, in addition to retaining the necessary characteristics of a binder, such as good elastomeric and strength characteristics, are sufficiently high in energy and sufficiently miscible with nitrate ester plasticizers.

SUMMARY OF THE INVENTION

It has been discovered that when an oxetane ring is asymmetrically substituted at the 3-position with an azidomethyl ($-CH_2N_3$) substituent and a nitratomethyl ($-CH_2ONO_2$) substituent, a highly energetic oxetane compound is produced. In particular, this oxetane compound is useful as a monomer in the preparation of polyethers which may be subsequently cured to form energetic binder materials useful in energetic formulations.

It has also been discovered that, unlike the homopolymerization of many oxetane monomers which give crystalline compounds, the homopolymerization of 3-azidomethyl-3-nitratomethyloxetane gives an amorphous oil which has a unique combination of thermal stability, chemical functionality and physical properties. These qualities make the AMNO homopolymer highly useful as elastomeric binders in high-energy propellant formulations.

It has further been discovered that 3-azidomethyl-3-nitratomethyloxetane can be copolymerized with other known energetic oxetane monomers to produce amorphous materials. The presence of 3-azidomethyl-3-nitratomethyl, even in small amounts, prevents crystallinity and provides copolymers which are amorphous in character.

The novel homopolymers and copolymers of the present invention, in addition to retaining the necessary characteristics of a binder, such as good elastomeric and mechanical strength properties, are sufficiently high in energy and sufficiently miscible with nitrate ester plasticizers to be useful as elastomeric binders in propellant formulations or the like.

Other advantages, objects, features and embodiments of the present invention will become apparent from the detailed description which follows.

DETAILED DESCRIPTION OF THE INVENTION AND PREFERRED EMBODIMENTS

The oxetane of the present invention has the formula:

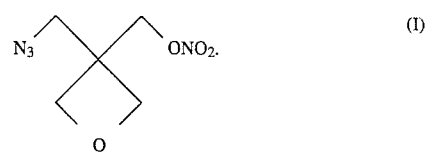

The oxetane of Formula I, 3-azidomethyl-3-nitratomethyloxetane (ANMO), is synthesized using 3-bromomethyl-3-hydroxymethyl oxetane (BMHMO) as the starting material. Reaction of 3-bromomethyl-3-hydroxymethyloxetane with sodium azide (NaN₃) in acetone or dimethylformamide (DMF) gives the corresponding 3-azidomethyl-3-hydroxymethyloxetane in essentially quantitative yield. Subsequent reaction of 3-azidomethyl-3-hydroxymethyloxetane with acetyl nitrate gives the oxetane AMNO.

The oxetane AMNO is particularly useful for polymerizing to form polyethers which may be subsequently cured to form energetic binder materials useful in energetic formulations. This oxetane monomer can be used to form either homopolymers or copolymers. When homopolymerized, the resulting polyethers have the formula:

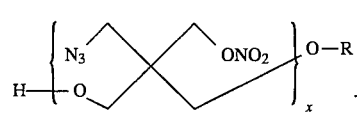

(II)

In Formula II, R is a fragment of the initiator which is incorporated into the polymer chain. More particularly, R is an initiator fragment including, but not limited to, H, $CH_3-$, $HO-(CH_2)_4-$, $CH_3C(CH_2OH)_2CH_2-$ and $C_2H_5C(CH_2OH)_2CH_2-$. In the above x is an integer having a value selected so that the homopolymer has a weight average molecular weight ranging from about 1,000 to about 100,000. Homopolymers of 3-azidomethyl- 3-nitratomethyloxetane having weight average molecular weights ranging from about 4,000 to about 25,000 are preferred. Homopolymers of 3-azidomethyl-3-nitratomethyloxetane having weight average molecular weights ranging from about 4,000 to about 12,000 are even more preferred.

Certain copolymers in accordance with the present invention are those having the general formula:

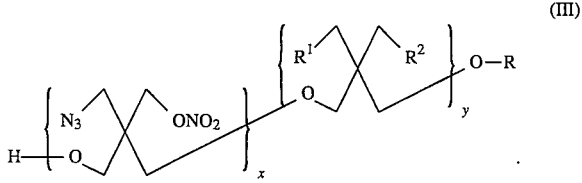

(III)

In Formula III, R is a fragment of the initiator which is incorporated into the polymer chain. More particularly, R is an initiator fragment including, but not limited to, H, $CH_3-$, $HO-(CH_2)_4-$, $CH_3C(CH_2OH)_2CH_2-$ and $C_2H_5C(CH_2OH)_2CH_2-$. Moreover, in Formula III, $R^1$ and $R^2$ are independently selected and may be functional groups including, but not limited to, H, lower alkyl, $NF_2$, $ONO_2$, $NO_2$, $N_3$, and $N(R^3)NO_2$, where $R^3$ is H or a lower alkyl. The term "independently selected" is used herein to indicate that the two R groups, $R^1$ and $R^2$, may be identical or different. The term "alkyl" is used herein to refer to substituents that are monovalent aliphatic hydrocarbon radicals. The alkyl groups may be straight-chain or branched-chain, limited only by steric hinderance. Additionally, since alkyl groups do not add to the energetic character of the molecule, shorter alkyl groups (i.e., 1–4 carbons) and saturated alkyl groups are preferred. The indexes, x and y, in Formula III are integers having values selected so that the copolymer has a weight average molecular weight ranging from about 1,000 to about 100,000.

Within the scope of Formula III, certain copolymers are preferred, namely those in which $R^1$ and $R^2$ are independently either $ONO_2$ or $N_3$; and x and y are integers having values such that the copolymer has a weight average molecular weight ranging from 2,000 to 50,000. Further preferred are copolymers in which $R^1$ and $R^2$ are both $ONO_2$; and x and y are integers having been selected so that the copolymer has a weight average molecular weight ranging from about 4,000 to about 25,000. Also preferred are copolymers in which $R^1$ and $R^2$ are both $N_3$; and x and y are integers having been selected so that the copolymer has a weight average molecular weight ranging from about 4,000 to about 25,000.

Further copolymers, in accordance with the present invention, are those formed from AMNO and at least one other oxetane monomer unit(s), in any proportion, order or arrangement. The oxetane monomer unit(s), other than AMNO, in unpolymerized form has the general formula:

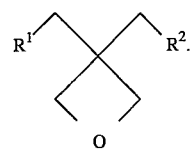

(IV)

In above formula, $R^1$ and $R^2$ are members independently selected from the group consisting of H, lower alkyl, $NO_2$, $ONO_2$, $N_3$, and $N(R^3)NO_2$, where $R^3$ is H or a lower alkyl. Examples of oxetanes used to form copolymers with AMNO in accordance with the invention include, but are not limited to, the following:

| | |
|---|---|
| BEMO | 3,3-bis-(ethoxymethyl)oxetane, |
| BCMO | 3,3-bis-(chloromethyl)oxetane, |
| BMMO | 3,3-bis-(methoxymethyl)oxetane, |
| BFMO | 3,3-bis-(fluoromethyl)oxetane, |
| HMMO | 3-hydroxymethyl-3-methyloxetane, |
| BAOMO | 3,3-bis-(acetoxymethyl)oxetane, |
| BHMO | 3,3-bis-(hydroxymethyl)oxetane, |
| OMMO | 3-octoxymethyl-3-methyloxetane, |
| CMMO | 3-chloromethyl-3-methyloxetane, |
| AMMO | 3-azidomethyl-3-methyloxetane, |
| BIMO | 3,3-bis-(iodomethyl)oxetane, |
| IMMO | 3-iodomethyl-3-methyloxetane, |
| PMMO | 3-propynomethyl-3-methyl oxetane, |
| NMMO | 3-nitratomethyl-3-methyloxetane, |
| DMMO | 3-difluoroaminomethyl-3-methyloxetane, |
| BDMO | 3,3-bis-(difluoroaminomethyl)oxetane, |
| BMNAMO | 3,3-bis-(methylnitratomethyl)oxetane, |
| MNAMMO | 3-methylnitratomethyl-3-methyloxetane, and |
| BAMO | 3,3-bis-(azidomethyl)oxetane. |

Within the scope of Formula IV, certain oxetane monomer units are preferred, namely those in which $R^1$ and $R^2$ are both $ONO_2$, i.e., the oxetane monomer unit is 3,3-bis-(nitratomethyl)oxetane (BNMO), or those in which $R^1$ and $R^2$ are both $N_3$, i.e., the oxetane monomer unit is 3,3-bis-(azidomethyl)oxetane (BAMO).

Certain of these copolymers are preferred, namely those copolymers comprising between about 5 to about 95 molar percent of AMNO and about 5 to about 95 molar percent of at least one other oxetane monomer unit(s). Also preferred are copolymers comprising between about 30 to about 65 molar percent of AMNO and about 35 to about 70 molar percent of at least one other oxetane monomer unit(s). Further preferred are copolymers comprising between about 10 to about 20 molar percent of AMNO and between about 80 to about 90 molar percent of at least one other oxetane monomer unit(s). Even furthered preferred are copolymers comprising between about 10 to about 20 molar percent of AMNO and between about 80 to about 90 molar percent of either BAMO or BNMO.

Additionally, copolymers, made up of AMNO and at least one other oxetane monomer unit(s), having weight average molecular weights ranging from about 2,000 to about 25,000 are preferred. Further preferred are copolymers, made up of AMNO and at least one other oxetane monomer unit(s), having weight average molecular weights ranging from about 4,000 to about 12,000.

Since propellants and explosives are preferably elastomeric in character, structures, both polymeric and non-polymeric, which are amorphous in character are preferred over those that are crystalline. In the present invention, this is achieved by asymmetrically substituting the oxetane ring at the 3-position with an azidomethyl substituent and a nitratomethyl substituent. One of the primary advantages of 3-azidomethyl- 3-nitratomethyloxetane is that it is an amorphous oil that has very useful thermal stability, chemical functionality and physical properties.

Copolymers are generally advantageous relative to homopolymers because the presence of an additional oxetane monomer unit(s), even in small amounts, substantially reduces chain regularity. Homopolymers having a high degree of chain regularity exhibit substantial chain folding, resulting in a compact structure which tends to be crystalline or highly viscous. However, unlike the homopolymerization of many oxetane monomers, the homopolymerization of 3-azidomethyl-3-nitratomethyloxetane gives a polymer which is amorphous in character and which exhibits a unique combination of thermal stability, chemical functionality and physical properties. Due to the asymmetrical substitution of this monomer, the polymer backbone contains random asymmetry which prevents crystallinity. These AMNO homopolymers are very useful in forming energetic binders for propellant formulations or the like.

Furthermore, 3-azidomethyl-3-nitratomethyloxetane can be copolymerized with other known energetic oxetane monomers. Frequently, existing high-energy oxetane monomers which have identical groups on the 3-position, such as 3,3-bis-(azidomethyl)oxetane (BAMO) or 3,3-bis-(nitratomethyl)oxetane (BNMO), give crystalline polymers which are not useful in binder applications. In order to obtain amorphous materials suitable for use as elastomeric binders, mono-energetically substituted monomers, such as 3-azidomethyl-3-methyloxetane or 3-nitratomethyl-3-methyloxetane, have been added to give copolymers which are amorphous in character, but which have diminished energy content. 3-Azidomethyl-3-nitratomethyl oxetane, however, can be used to form amorphous copolymers with monomers such as BAMO and BNMO without compromising the energy content. The presence of even small amounts (e.g., 5 to 20%) of the asymmetrically substituted 3-azidomethyl-3-nitratomethyloxetane monomer will be sufficient to produce amorphous polymers with monomers that usually give crystalline homopolymers, such as BAMO and BNMO.

Oxetane compounds can be synthesized using a variety of different methods. The methods used vary depending upon the oxetane compounds desired. 3-Bromomethyl- 3-hydroxymethyl oxetane (BMHMO), for example, is a convenient and inexpensive route for the preparation of 3,3-asymmetrically di-substituted oxetane compounds. Reaction of 2,2-bis-(bromomethyl)propane-1,3-diol (i.e., neopentyl glycol dibromide) with base coreactants, such as sodium ethoxide in ethanol, gives BMHMO. Additionally, BMHMO can be obtained from the reaction of neopentyl glycol dibromide with sodium hydroxide in dimethylformamide (DMF), sodium hydroxide in dimethylsulfoxide, sodium or potassium hydroxide in ethanol, and by neat reaction with fused potassium hydroxide. Once formed, BMHMO can be used as the starting point for a large number of energetic, asymmetrically di-substituted oxetanes. Oxetanes containing energetic pendant groups such as azido, nitrato, nitro, difluoroamino, nitroamino, dinitramino, cubyl and carboranyl can be synthesized using BMHMO as starting material. Table I lists examples of structures that can be synthesized using BMHMO as starting material.

TABLE I

Asymmetrically Di-substituted Oxetanes

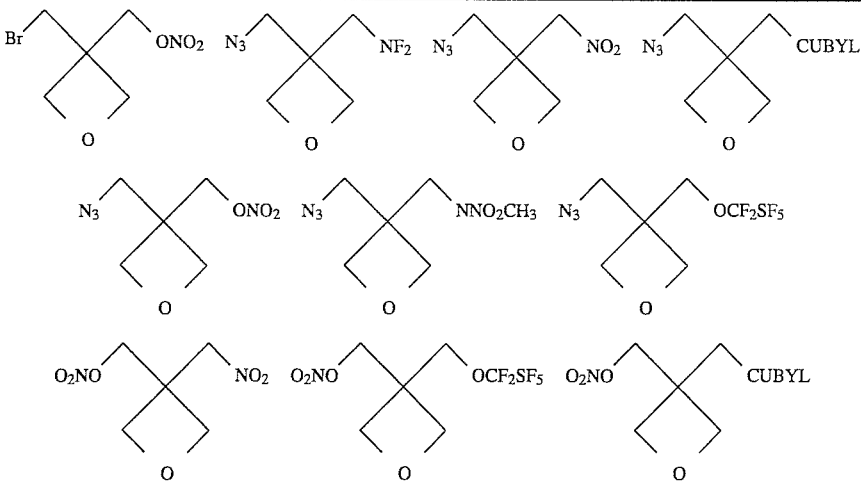

TABLE I-continued

Asymmetrically Di-substituted Oxetanes

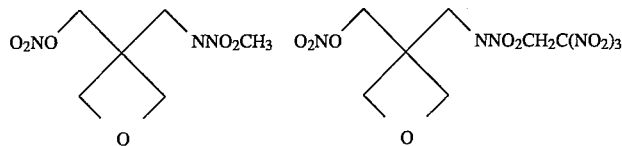

The polymers of the present invention may be prepared in accordance with conventional procedures. Polyethers are formed from the oxetane monomers using standard cationic polymerization reactions. Such reactions employ an initiator formed from a hydroxy compound, i.e., a preinitiator precursor, and a catalyst for cationic polymerization (e.g., a Lewis acid catalyst). Such hydroxy compounds include, but are not limited to, water and mono- and polyhydric alcohols, such as methanol, butane-1,4-diol, propane-1,3-diol, trifluoroethanol, trimethylolethane, trimethylolpropane and pentaerythritol It will be understood by those of skill in the art that the number of functional hydroxy groups on the hydroxy compound generally determines the functionality of the polymer chain with grows therefrom; thus, a diol will give rise to a difunctional polymer, a triol to a trifunctional polymer, etc. Suitable catalysts include, but are not limited to, boron trifluoride etherate, boron trifluoride, fluoroboric acid, or aluminum, phosphorous and antimony halides. The initiator reacts with one of the available oxetane monomers to form an initiating species, and polymerization proceeds by chain elongation until substantial, e.g., greater than about 95%, exhaustion of the monomers.

More specifically, polymerization of the oxetane monomers occurs by a cationic ring-opening reaction. The mechanism for the cationic ring-opening reaction is set forth below:

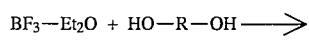

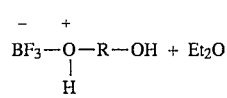

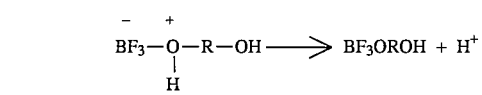

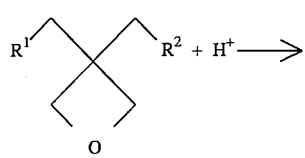

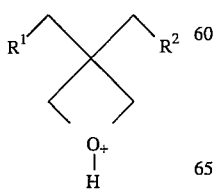

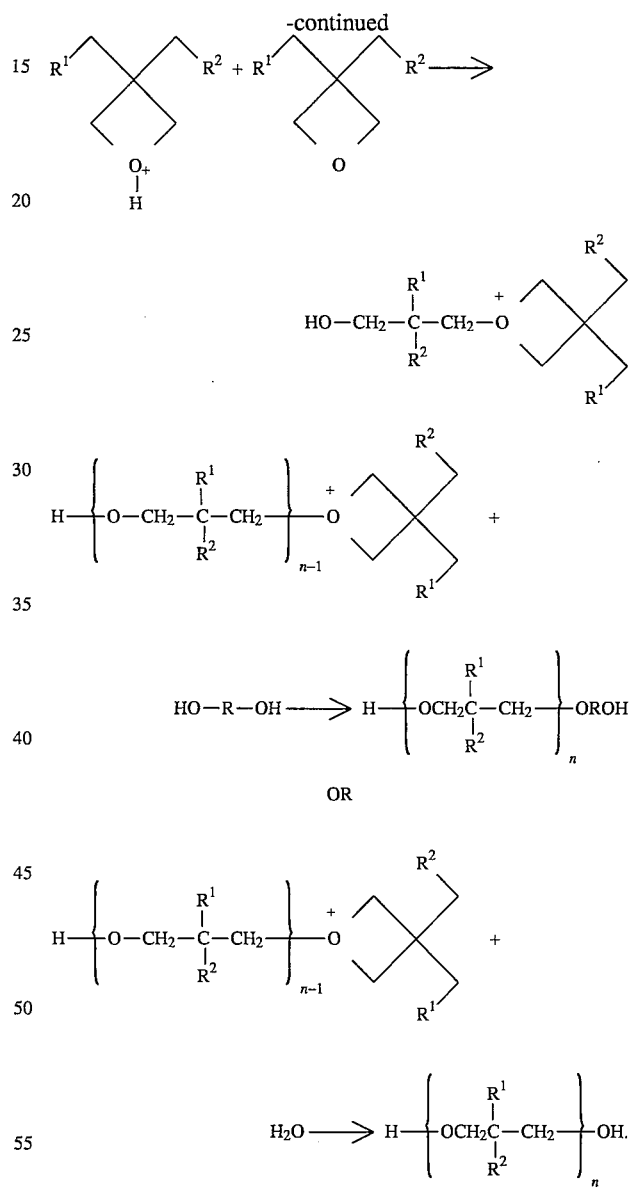

Briefly, polymerization is initiated by the proton donated by the initiator and the protonated oxetane ring undergoes propagation with other oxetane monomers to generate the polymer chain. The growing polymer is then terminated either with alcohol or water to give the hydroxy-terminated polymers of the present invention. It should be noted that the polymers of the present invention are generally a mixture of polymers resulting from both alcohol and water terminations.

Any solvent known to be compatible with cationic polymerization with respect to solubility of reactants, stability of the cation formed, etc., may be used. In addition to the solvents used in the examples, suitable solvents include, but are not limited to, the following: methylene chloride, Freons, hydrocarbons, chloroform, methyl chloride, ethylene chloride, nitromethane and chlorinated aromatic hydrocarbons, such as, for example, cholorbenzene. In a presently preferred embodiment of the present invention, methylene chloride is the solvent used.

The length of the chains is largely dependent upon the molar equivalents of monomers (m) and the initiators (n). Generally, for use in propellant binders, polyether chains are prepared having molecular weights (weight average) of between about 2,000 and about 25,000. Distribution of monomer units throughout the polymer chains and polydispersity of the chains depends on specific polymerization conditions. Polyethers in accordance with the present invention generally have polydispersities between about 1.1 and about 2.5 and, more preferably, between about 1.3 and about 1.8. The molar ratio of monomer units in the formed polyether generally reflects the molar ratios of the available monomers, but may also depend upon the relative reactivities of the monomers in the polymerization reaction.

Through NMR analysis ($^1H/^{13}C$) of the polymers formed in accordance with the cationic ring-opening mechanism set forth above, it has been determined that the initiator fragment, e.g., butane-1,4-diol, is incorporated at the end of the polymer chain and not in the middle of the polymer backbone. The NMR data ($^1H/^{13}C$) clearly shows the presence of a —$CH_2CH_2CH_2CH_2OH$ group which can only occur if the butane-1,4-diol fragment is incorporated at the end of the polymer chain. If the butane-1,4-diol fragment were incorporated into the middle of the polymer chain, two peaks corresponding to the symmetrical —$OCH_2CH_2CH_2CH_2O$— group would be present in the NMR data. The NMR data, however, do not indicate the presence of such a group. While in theory, the initiator fragment could be incorporated into the backbone of the polymer, it is highly unlikely that the bulky, high molecular weight polymer will compete efficiently as a chain terminator with a low molecular weight, highly mobile butane-1,4-diol. The foregoing findings are consistent with the findings of Conjecvaram, et al. (J. Polymer Science, 23:429–444 (1985)), wherein butane-1,4-diol is used as an initiator in conjunction with $BF_3$.etherate to polymerize unsubstituted oxetanes. The NMR data obtained by Conjecvaram, et al. also shows the presence of the —$CH_2CH_2CH_2CH_2OH$ group and, thus, indicates that the butane- 1,4-diol fragment is incorporated at the end of the polymer.

The polymers of the present invention are hydroxy-terminated, and thus they are curable with isocyanates through chain extension and cross-linkable to form elastomers. Polymeric chains which terminate at both ends with primary alcohol groups have a particular advantage since such groups are more reactive toward isocyanate groups during curing than the corresponding secondary and tertiary hydroxyl end groups. Elastomers are formed from the polyethers of the present invention by curing with isocyanates having a functionality of at least two, e.g., toluene diisocyanate. To promote chain elongation, at least one equivalent of an isocyanate is required. Preferably, cross-linking is also promoted by using an isocyanate of higher functionality or by adding a separate crosslinking agent, such as trimethylolethane or trimethylolpropane.

The invention will be described in greater detail by way of specific examples. The following examples are offered for illustrative purposes, and are intended neither to limit or define the invention in any manner.

EXAMPLE I

This example illustrates the preparation and properties of 3-azidomethyl-3-nitratomethyloxetane.

A. Preparation Of 3-Bromomethyl-3-hydroxymethyloxetane

Sodium ethoxide in ethanol (21%, 185.74 g, 0.573 mol) was added over a period of 10 min to a solution of 2,2-bis-(bromomethyl)propane-1,3-diol (150 g, 0.573 mol) in 650 mL of ethanol. This solution was refluxed for 2 h, stirred at ambient temperature for 16 h, filtered and then evaporated to give an oil containing solids. The resulting residue was dissolved in 200 mL of methylene chloride, filtered and evaporated to give 98 g of crude oxetane. An analytical sample was purified by distillation at 113° C. and 3-mm pressure. 52.95 g, representing a 52 % yield, of 3-bromomethyl-3-hydroxymethyl oxetane were obtained. NMR: $^1H$ NMR 3.75 (s, 2 H), 3.88 (d, J=4.9 Hz, 2 H), 4.45 (s, 4 H); $^{13}C$ NMR 36.336 (t, J=152.78 Hz), 45.0935 (s), 63.995 (t, J=143.3 Hz), 77.216 (t, J=152.78 Hz).

B. Preparation of 3-Azidomethyl-3-hydroxymethyloxctane

A mixture of sodium azide (9.5 g, 0.14 mol), 3-bromomethyl-3-hydroxymethyloxetane (24.0 g, 0.14 mol), 20 mL of acetone and 20 mL of water was refluxed for 12 h. The acetone was evaporated and the resulting residue was extracted with two portion of 40 mL of ethyl acetate. The combined organic extracts were dried over magnesium sulfate ($MgSO_4$). The solvent was removed by evaporation. 18.0 g, representing a 94% yield, of 3-azidomethyl-3-hydroxymethyloxetane were obtained as an oil. This oil was found to be essentially pure by gas-liquid chromatography (GLC) analysis. NMR: $^1H$ NMR 3.70 (s, 2 H), 3.84 (d, J=4.9 Hz, 2 H), 4.44 (s, 4 H); $^{13}C$ NMR 44.283, 53,852, 64,073, 76.227.

C. Preparation of 3-Azidomethyl-3-nitratomethyloxetane

Nitric acid (100%, 2.65 g, 42 mmol) was added dropwise to acetic anhydride (4.73 g, 45 mmol), and the solution was stirred for 10 min and cooled to 0° C. A solution of 3-azidomethyl-3-hydroxymethyloxetane (5.0 g, 35 mmol) in 13 mL of methylene chloride was added over a period of 10 min, and then the solution was stirred for 30 min. The reaction mixture was washed with 10% aqueous sodium hydroxide, filtered and evaporated to 4.5 g, representing a 68% yield, of 3-azidomethyl-3-nitratomethyloxetane as a slightly yellow oil. Differential scanning calorimetry (DSC) showed an onset of decomposition at 206.4° C., and a maximum at 221.4° C.; Heat Flow: 279 Joules/g; NMR: $^1H$ NMR 3.75 (s, 2 H), 4.43 (d, J=6.9 Hz, 2 H), 4.46 (d, J= 6.9 Hz, 2 H), 4.69 (s, 2 H); $^{13}C$ NMR 41.875, 53.947, 72.864, 75.583.

EXAMPLE II

This example illustrates the preparation and properties of the homopolymer poly(3-azidomethyl-3-nitratomethyloxetane).

A. Preparation of Poly(3-azidomethyl-3-nitratomethyloxetane)

A solution of butane-1,4-diol (24 mg, 0.266 mmol) and boron trifluoride etherate (77.9 mg, 0.548 mmol) in methylene chloride (1.26 g) was stirred at ambient temperature for 15 min under nitrogen in a dry polymerization flask. The solution was cooled to 8° C. and then a solution of 3-azidomethyl-3-nitratomethyloxetane (1.00 g, 5.32 mmol) in methylene chloride (1.32 g) was added over a period of 10 min. The resulting solution was stirred for 1 h at 10° C. at which time $^1$H NMR analysis of an aliquot indicated that the reaction was 53% complete. The solution was warmed to ambient temperature, stirred 16 h, and quenched with 0.1 mL of water. 20 mL of methanol were added and the organic layer was decanted from the polymer that had precipitated as an oil. The oil was washed with methanol and dried for 24 h in vacuo (2 mm) to give 0.75 g, representing a 75% yield, of poly(3-azidomethyl-3-nitratomethyloxetane), as an amorphous oil. Differential scanning calorimetry showed an onset of decomposition at 175° C., and a maximum at 215° C.; Heat Flow: 440 Joules/g; Gel Permeation Chromatography (GPC): Number Average Molecular Weight ($M_n$) 4,368, and Weight Average Molecular Weight ($M_w$) 6,320; Polydispersity (Disp.): 1.47; NMR: $^1$H NMR 3.39–3.45 (m, 6 Hz), 4.45 (s, 2 Hz).

In the above example, Gel Permeation Chromatography (GPC) was conducted on a Waters Gel Permeation Chromatograph equipped with four ultrastyragel columns (100 Å, 500 Å, $10^3$ Å and $10^4$ Å), a differential refractive index detector and a Data Module 730. THF was used as the mobile phase. The GPC was calibrated with a series of well characterized (i.e., $M_n$ and $M_w$ are well known) polystyrene standards (narrow standards) and, thus, the number average molecular weight ($M_n$) and the weight average molecular weight ($M_w$) reported above are expressed relative to polystyrene.

The foregoing is offered primarily for purposes of illustration. It will be readily apparent to those skilled in the art that the operating conditions, materials, procedural steps and other parameters of the systems described herein may be furthered modified or substituted in various ways without departing from the spirit and scope of the invention.

What is claimed is:

1. A polymer formed by the cationic polymerization of a compound having the formula

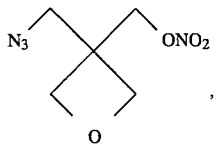

, said polymer having a weight average molecular weight ranging from about 1,000 to 100,000.

2. A polymer in accordance with claim 1 having a weight average molecular weight ranging from about 2,000 to about 50,000.

3. A polymer in accordance with claim 1 having a weight average molecular weight ranging from about 4,000 to about 25,000.

4. A polymer formed from the cationic polymerization of 3-azidomethyl- 3-nitratomethyloxetane and at least one other oxetane monomer unit(s), said other oxetane monomer unit(s) having the general formula:

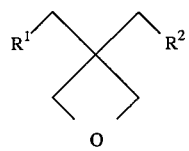

in which:

$R^1$ and $R^2$ are members independently selected from the group consisting of H, lower alkyl, $NO_2$, $ONO_2$, $N(R^3)NO_2$, where $R^3$ is H or a lower alkyl, and $N_3$;

wherein:

said polymer comprises between about 5 to about 95 molar percent of 3-azidomethyl- 3-nitratomethyloxetane and between about 5 to about 95 molar percent of at least one other oxetane monomer unit(s); and said polymer has a weight average molecular weight ranging from about 1,000 to 100,000.

5. A polymer is accordance with claim 4 in which:

$R^1$ and $R^2$ of said other oxetane monomer unit are both $ONO_2$.

6. A polymer in accordance with claim 4 in which:

$R^1$ and $R^2$ of said other oxetane monomer unit are both $N_3$.

7. A polymer is accordance with claim 4 in which said polymer comprises between about 30 to about 65 molar percent of 3-azidomethyl-3-nitratomethyloxetane and between about 35 to about 70 molar percent of at least one other oxetane monomer unit(s).

8. A polymer is accordance with claim 4 in which said polymer comprises between about 10 to about 20 molar percent of 3-azidomethyl-3-nitratomethyloxetane and between about 80 to about 90 molar percent of at least one other oxetane monomer unit(s).

9. A polymer is accordance with claim 8 in which:

$R^1$ and $R^2$ of said other oxetane monomer unit are both $ONO_2$.

10. A polymer in accordance with claim 8 in which:

$R^1$ and $R^2$ of said other oxetane monomer unit are both $N_3$.

11. A polymer is accordance with claim 4 having a weight average molecular weight ranging from about 2,000 to about 50,000.

12. A polymer is accordance with claim 4 having a weight average molecular weight ranging from about 4,000 to about 25,000.

13. A polymer is accordance with claim 4 having a weight average molecular weight ranging from about 4,000 to about 12,000.

14. A polymer having the formula

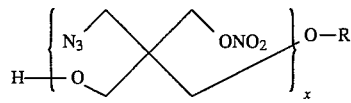

in which:

R is a member selected from the group consisting of H, $CH_3$—, $HO$—$(CH_2)_4$—, $CH_3C(CH_2OH)_2CH_2$— and $C_2H_5C(CH_2OH)_2CH_2$—; and x is an integer having a value selected such that said homopolymer has a weight average molecular weight ranging from about 1,000 to 100,000.

15. A polymer in accordance with claim 14 in which:
x is an integer having a value selected such that said homopolymer has a weight average molecular weight ranging from about 2,000 to about 50,000.

16. A polymer in accordance with claim 14 in which:
x is an integer having a value selected such that said homopolymer has a weight average molecular weight ranging from about 4,000 to about 25,000.

17. A polymer having the formula

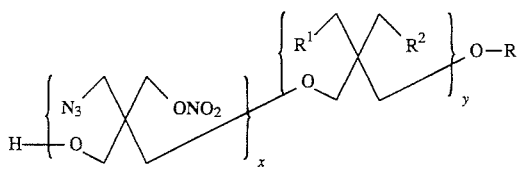

in which:
R is a member selected from the group consisting of H, $CH_3$—, $HO$—$(CH_2)_4$—, $CH_3C(CH_2OH)_2CH_2$— and $C_2H_5C(CH_2OH)_2CH_2$—;

$R^1$ and $R^2$ are members independently selected from the group consisting of H, lower alkyl, $NF_2$, $ONO_2$, $NO_2$, $N_3$, and $N(R^3)NO_2$, where $R^3$ is H or a lower alkyl; and x and y are integers such that said copolymer has a weight average molecular weight ranging from about 2,000 to about 25,000.

18. A polymer in accordance with claim 17 in which:
$R^1$ and $R^2$ are both $ONO_2$; and
x and y are integers such that said copolymer has a weight average molecular weight ranging from about 4,000 to about 25,000.

19. A polymer in accordance with claim 17 in which:
$R^1$ and $R^2$ are both $N_3$; and
x and y are integers such that said copolymer has a weight average molecular weight ranging from about 4,000 to about 25,000.

* * * * *